United States Patent [19]

Mecikalski

[11] Patent Number: 5,483,954
[45] Date of Patent: Jan. 16, 1996

[54] INHALER AND MEDICATED PACKAGE

[76] Inventor: Mark B. Mecikalski, 7580 N. Calle Sin Desengano, Tucson, Ariz. 85718

[21] Appl. No.: 258,743

[22] Filed: Jun. 10, 1994

[51] Int. Cl.⁶ .................................................. A61M 15/00
[52] U.S. Cl. ................ 128/203.15; 128/203.12; 128/200.24
[58] Field of Search .................. 128/203.15, 203.19, 128/203.21, 203.23, 203.24, 203.12, 200.24; 604/58; 222/636

[56] References Cited

U.S. PATENT DOCUMENTS

| | | | |
|---|---|---|---|
| 2,436,878 | 3/1948 | Biederman | 128/203.24 |
| 2,549,303 | 4/1951 | Friden | 128/206 |
| 2,642,063 | 6/1953 | Brown | 128/203.15 |
| 2,672,865 | 3/1954 | Willis | 128/203.15 |
| 3,918,451 | 11/1975 | Steil | 128/203.21 |
| 3,967,761 | 7/1976 | Melton, Jr. et al. | 128/203.21 |
| 4,846,168 | 7/1989 | Abiko et al. | |
| 5,035,237 | 7/1991 | Newell et al. | 128/203.15 |
| 5,042,472 | 8/1991 | Bunin | |
| 5,239,991 | 8/1993 | Chawla et al. | |
| 5,301,666 | 4/1994 | Lerk et al. | 128/203.15 |
| 5,349,947 | 9/1994 | Newhouse et al. | 128/203.21 |

FOREIGN PATENT DOCUMENTS

| | | | |
|---|---|---|---|
| 6078 | of 1913 | United Kingdom | 128/203.23 |
| 1118341 | 7/1968 | United Kingdom | 604/58 |
| 9204069 | 3/1992 | WIPO | 128/203.15 |

*Primary Examiner*—Edgar S. Burr
*Assistant Examiner*—V. Srivastava
*Attorney, Agent, or Firm*—Orgram & Teplitz

[57] ABSTRACT

An improved inhaler and medicated packet which uses a patient's breath to send powdered medication into the oral cavity of the patient. The inhaler is reusable and controls both the rate of airflow inside the chamber and prevents the patient from blowing into the inhaler. Disposable medicated packets are inserted into the inhaler. These medicated packets have preformed holes which pass air through the packet and entrain the medication. One inhaler can be used numerous times for numerous different types of medication. These medicated packets have a removable, protective layer to maintain the sterility and dryness of the measured dose of medication. In operation, the medication is transported from the packet, through the inhaler, and into the patient. The medicated packets are transparent on one side to allow the patient to observe if the medication has been completely delivered.

21 Claims, 3 Drawing Sheets

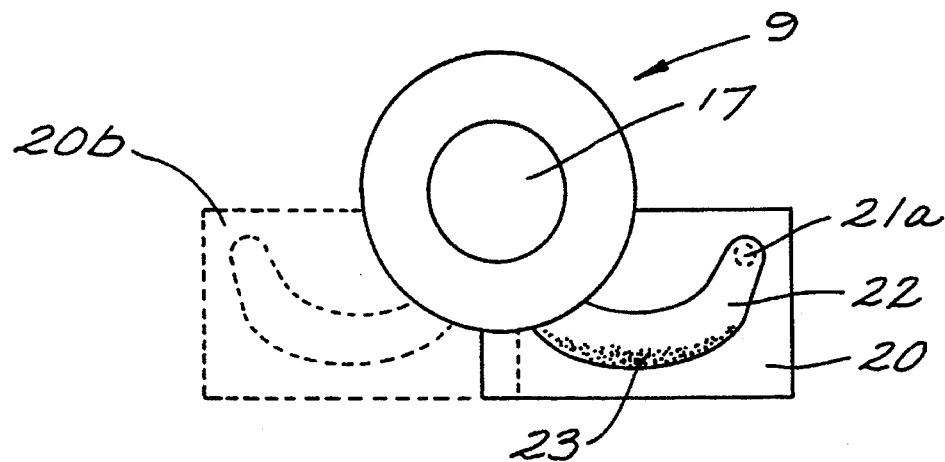
FIG. 5
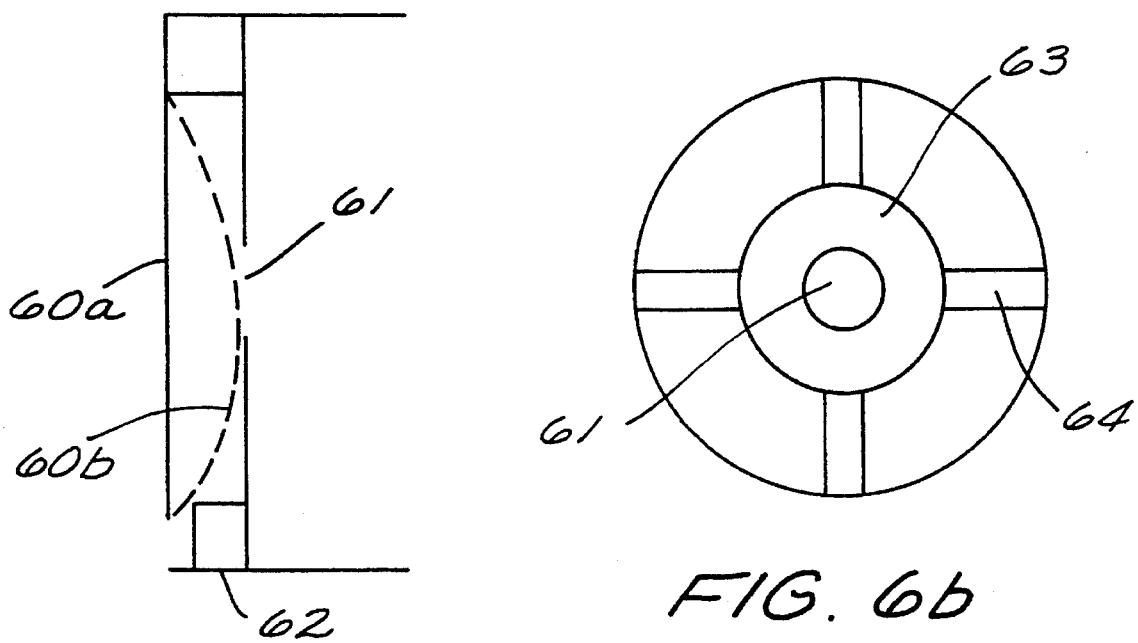
FIG. 6a
FIG. 6b

INHALER AND MEDICATED PACKAGE

BACKGROUND OF THE INVENTION

This invention relates to medical devices and particularly to inhalers and medicated packets.

Various devices have been proposed for delivering pharmaceutical preparations to the oral cavity. An early solution was to use a propellant to discharge powdered medication into the oral cavity of the patient. This has the drawback of the use of a propellant that could be harmful to the environment and aggravate a patient's preexisting bronchial problem.

To remedy this situation, inhalation devices which rely on the inhalation of the user have been proposed. One such device is described in U.S. Pat. No. 4,846,168, entitled "Inhaler" and issued to Abiko et al. on Jul. 11, 1989. Abiko's device, while eliminating the need for a propellent, has several draw backs. First, the drug is initially contained in a capsule which is opened by the apparatus through a breaking of the capsule. This creates a risk of accidental aspiration of capsule parts. Also, the medication is subject to handling and possible contamination prior to insertion in the device. The device also lacks any means to prevent the user from blowing back into the device, such as through a cough or sneeze, and ejecting the medication.

Additionally, the device is not designed to operate between a certain minimum and maximum flow rate and therefore, the Food and Drug Administration (FDA) requirement for dose variability is hard to meet.

Another proposed inhaler is described in U.S. Pat. No. 5,042,472 entitled "Powdered Inhaler Device" and issued to Bunin on Oct. 15, 1990. This device does not use capsulized medication, but still suffers from many of the drawbacks of the previously discussed inhaler of Abiko. Specifically, it lacks any way to prevent the user from blowing into the device, it is not designed to operate in a certain optimal range of airflow and it is difficult to tell if the user has inhaled all the medication. A further draw back is that the design of the mouthpiece makes it difficult to use.

A third inhaler is described in U.S. Pat. No. 5,239,991, entitled "Disposable Powder Medicant Inhalation Device with Peel-off Cover" and issued to Chawal et al., on Aug. 31, 1993. Like the previously discussed devices, this inhaler lacks a convenient way to tell if the medicine has been fully inhaled, it does not prevent the user from blowing into the inhaler and it is not designed to operate in a certain airflow range.

Additionally, neither Bunin's nor Chawal's device are reusable. While a disposable inhaler insures a sterile dose of medication, the design is inherently wasteful.

It is clear from the foregoing, that there is a need for an inhaler and medicated packet that is easy to use, that delivers an accurate dose, and that is efficient and economical, where the powdered medication is packaged in a disposable container and the inhaler is reusable.

SUMMARY OF THE INVENTION

The invention is an improved inhaler and medicated packet which uses a patient's breath to send powdered medication into the oral cavity of the patient. The inhaler is reusable and controls both the rate of airflow inside the chamber and prevents the patient from blowing into the inhaler. Because the inhaler is reusable, one inhaler can be used numerous times for numerous different types of medication.

Disposable medicated packets containing powdered pharmaceutical preparations are inserted into the inhaler. These medicated packets have preformed holes which pass air through the packet and entrain the medication. Additionally, these medicated packets have a removable, protective layer to maintain the sterility and dryness of the measured dose of medication.

In operation, the medication is transported from the packet, through the inhaler, and into the patient. The medicated packets are transparent on one side to allow the patient to observe if the medication has been completely delivered.

In its preferred embodiment, the user of the inhaler first removes the protective cap from the inhaler and places the cap on the end of the inhaler.

The user then takes a medicated packet, which contains the powdered medication and removes the protective layer, exposing the holes located on the packet. The medicated packet is inserted into a slot, located, in the preferred embodiment, on the bottom or side of the inhaler, in such a way that at least one hole is inside the inhaler and one hole is outside.

After the medicated packet is inserted into the inhaler, the user places his mouth around the mouthpiece and inhales. Air enters holes located around the end of the inhaler. The air travels through a first valve designed to limit the flow of air. As the air rushes through the valve, and into the inside of the inhaler, it causes air to flow through the packet and entrain the medicine into the inside of the inhaler.

Once so entrained, the powdered medication and the air travel through an inner chamber designed to produce turbulent flow so as to ensure the even breakup of the powdered medication. The medicated airstream flows past a check valve, designed to prevent reverse airflow, through the mouthpiece and into the user's bronchial and lung area.

The packet is designed such that one side is transparent. This allows the user to monitor the removal of the medication easily.

An important aspect of this invention is that it permits different medicated packets to be inserted into the same inhaler. This aspect is important since it allows one inhaler to be used multiple times for multiple types of medication while maintaining the sterility of the medication.

A valve is incorporated to limit the maximum airflow. This aspect is important since it allows the inhaler to meet Food and Drug Administration (FDA) requirements for dosage variabilities. This valve is located upstream of the point of powder entrance into the inhaler, to keep from getting clogged with powder and malfunctioning.

The invention includes a check valve to prevent the user from blowing into the inhaler, through a cough or a sneeze, and discharging the medicine.

The invention has a great deal of usefulness in the medical and pharmaceutical field, where a reusable, efficient, easy to use inhaler and medicated packet that provides a way to monitor the administration of medicine is needed.

It is well known that many powder inhalers deliver medication to the lungs in a flow rate dependent fashion. That is, the higher the flow rate through the inhaler, the more the powder is disaggregated into fine particles able to reach the lungs. Because patients may inhale at different flow rates, this means that the dose to the lung may vary depending on how fast the patient inhales. The FDA has found a high degree of dose variability unacceptable, and this has prevented the acceptance of new powder inhalers in the United States. One way to solve this problem is to have the inhaler operate in a narrow range of flow rates, so the dose of finely divided powder reaching the lungs falls within a similarly narrow range.

Human physiology must be allowed for in the design. Since many patients with lung disease are children, and cannot achieve high flows, a reasonable range of operation for children and adults is 20 to 35 liters per minute. Interestingly, although children cannot achieve high flows, they can achieve high inspiratory pressure differentials at low flow rates, in many cases, as high as adults.

This design, then, represents a low flow, high resistance inhaler, suitable for adults and children, and it is designed to operate in a rather narrow flow range.

The lower limit of the flow range is determined by visual observation of the powder through the clear portion of the blister. If the medication is not inhaled out of the blister, the patient knows the minimum flow rate has not been met and they must inhale harder. With a little practice they can easily exceed the minimum flow rate every time.

The maximum flow rate is determined by two factors. One is the valve, limiting airflow, which increases its resistance as inspiratory pressure increases. The other is the fact that humans are limited in the inspiratory pressure they can generate over the flow range, with the maximum being about 50 cm of water.

The invention, together with various embodiments thereof, will be more fully illustrated by the accompanying drawings and description.

DRAWINGS IN BRIEF

FIG. 5 is a view from a user's perspective of the inhaler with packet installed.

FIG. 6a is a cutaway view of the preferred embodiment of the flow limiting valve.

FIG. 6b is a detailed view of an alternative embodiment of the flow limiting valve.

DRAWINGS IN DETAIL

Figure 1A:
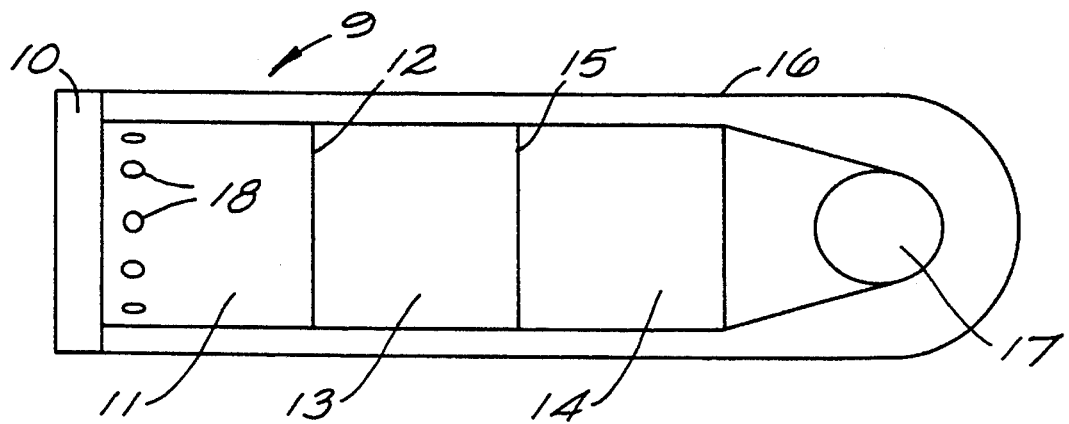
FIG. 1a is a plan view of the inhaler with cap in place.

FIG. 1a is a plan view of the inhaler with cap in place.

The inhaler 9 consists of: an endpiece 10, a first valve section 11, having holes around it 18, a middle inner chamber section 13, a second valve section 14 and a mouthpiece 17. A cap 16 covers the inhaler.

During operation, residue from the powdered medication tends to build up in the middle inner chamber section 13 and the second valve section 14. Additionally, it is advisable to clean mouthpiece 17 prior to each use to prevent the spread of disease. To clean these sections, inhaler 9 comes apart at 12 and 15, so that each section can be washed and cleaned prior to the next use.

Figure 1B:
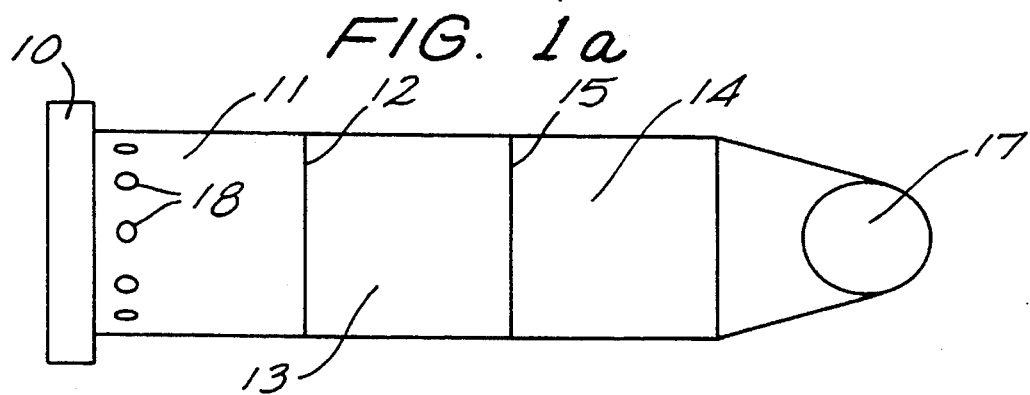
FIG. 1b is a plan view of the inhaler with the cap removed.
Figure 1B:
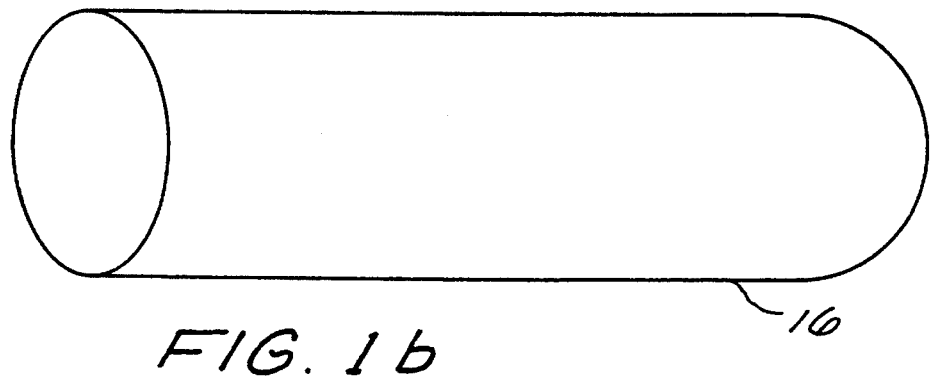

FIG. 1b is a plan view of the inhaler 9 showing the cap 16 removed. The cap 16 is placed over the inhaler 9 when the inhaler 9 is not in use to protect the inhaler 9 and prevent contamination. Prior to using the inhaler 9, the cap 16 is removed.

Figure 1C:
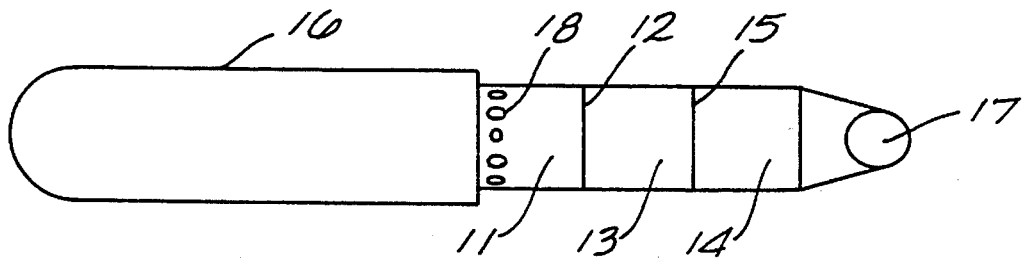
FIG. 1c is a plan view of the inhaler with the cap stored over the endpiece.

FIG. 1c is a plan view of the inhaler 9 with the cap 16 stored over the endpiece 10. The cap 16 is placed over the endpiece 10 to prevent loss of the cap 16 when the inhaler 9 is being used.

Figure 2A:
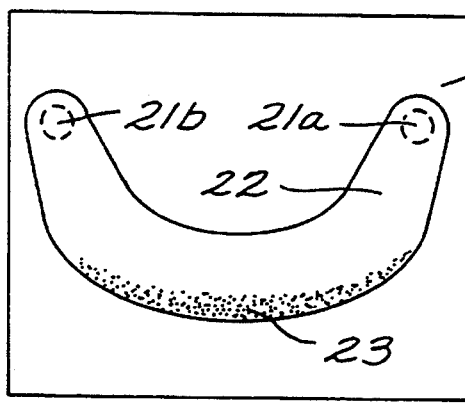
FIGS. 2a, 2b, 2c are front, back, and side views, respectively, of the medicated packet.

FIG. 2a is a front view of the medicated packet 20. The medicated packet 20 has a raised envelope 22 which contains the powdered medication 23. At least two holes 21a and 21b are located on the other side, at either end of the envelope 22, such that air flows in one hole 21a, through the envelope 22, and out the other hole 21b.

Figure 2B:
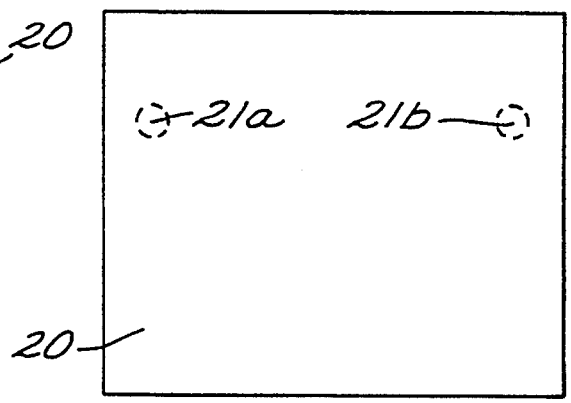

FIG. 2b is a view of the back of the medicated packet 20, showing two holes 21a and 21b. Any number of holes could be used, but only two are pictured here. These holes lead to the envelope (not pictured) which contains the powdered medication (also not pictured).

Figure 2C:
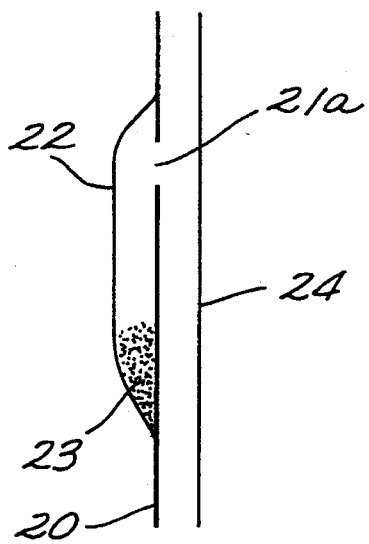

FIG. 2c is a side view of the medicated packet 20. This view shows the removable layer 24 removed, which, when in place, covers the holes 21a and 21b in order to contain the powdered medication 23 prior to use and to maintain the sterility and dryness of the powdered medication 23 contained in the envelope 22. This allows for a dose of powdered medication 23 to be delivered that is not contaminated through prior handling.

Figure 3:
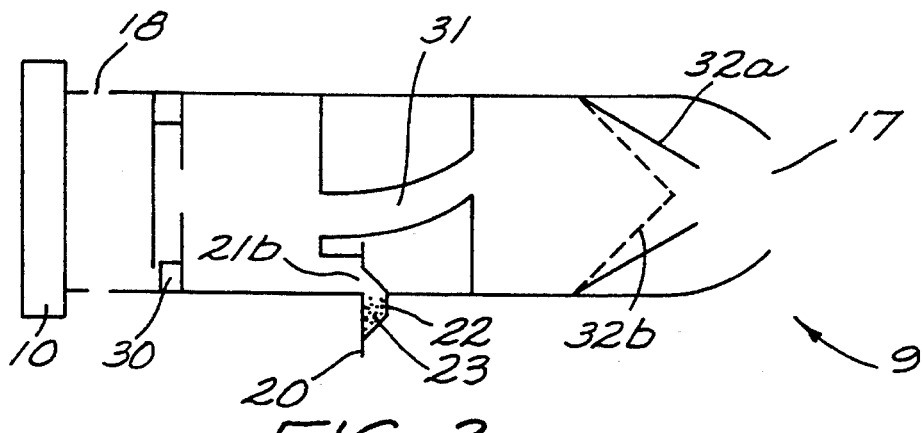
FIG. 3 is a detailed cutaway view of the inhaler with the packet installed.

FIG. 3 is a detailed, cutaway view of the preferred embodiment of the invention.

This view shows the first valve 30, the inner chamber 31, and the second valve 32a, 32b. The packet 20 with the powdered medication 23 is attached to the bottom. Although the embodiment has a slot at the bottom for insertion of the packet 20, those of ordinary skill in the art readily recognize that the slot for the packet is possible on the side or even the top o the inhaler.

At one end is the mouthpiece 17 and at the other end is the endpiece 10.

In operation, the user places his lips over the mouthpiece 17 and inhales. Air enters through holes 18, located around the inhaler near the first valve 30. After entering the holes 18, the air travels through the first valve 30 which controls the maximum amount of airflow in the inhaler. The air flows inside the inhaler towards the inner chamber 31. As the air flows towards the inner chamber, it causes air to flow inside packet 20, entraining the powdered medication 23 and causing it to exit out one of the holes 21b in the packet 20. The powdered medication 23 is now in the airflow of the inhaler 9.

The air and the powdered medication 23 travels through the inner chamber 31. The inner chamber 31 is essentially spiral or circular shaped. This creates a turbulent airflow and abrasion against the chamber walls and ensures that the powdered medication 23 is disaggregated into fine particle, able to penetrate the lung. In this context, curving is meant to include both spiral and circular pathways.

The air and powdered medication 23 next passes through an open second valve 32a. The second valve 32a is essentially a check valve which allows flow towards the mouthpiece 17 but not in the opposite direction. When air flows towards the mouthpiece, the valve is open 32a. When the user blows into the mouthpiece 17, such as through a cough or sneeze, the second valve closes 32b, preventing air from flowing back into the inhaler 9 and discharging the powdered medication 23 out the packet.

After passing through the open second valve 32a, the powdered medication 23 travels through the mouthpiece 17 and into the user.

Figure 4:
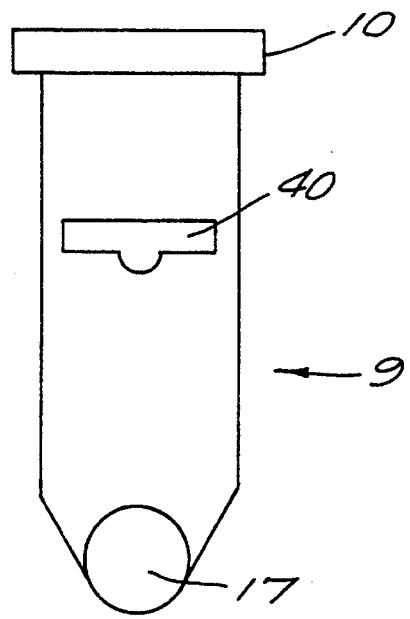
FIG. 4 is a view of the bottom of the inhaler.

FIG. 4 is a bottom view of the inhaler 9. This view shows the endpiece 10, the mouthpiece 17 and the slot 40, where the medicated packet is inserted. Slot 40 is positioned downstream from the first valve such that air flow is initiated and regulated before reaching the medicated packet and upstream from the second valve so any reverse airflow is stopped before reaching the medicated packet.

FIG. 5 shows a view from the perspective of the user of the inhaler 9 with the medicated packet 20 inserted. An alternative embodiment, the medication packet 20b can be inserted on the other side of the inhaler 9. As can be seen in FIG. 5, one of the holes 21a, is outside the inhaler 9 and the other hole, not pictured in this view, is inside the inhaler 9. In operation, when a user inhales through mouthpiece 17, the air flows into hole 21a, outside the inhaler, through the envelope 22, picking up the powdered medication 23 and exiting out the second hole (not pictured) inside the inhaler. During application of the medication, the user observes the amount of medication remaining by looking at the envelope 22, which is transparent.

In an alternative embodiment, the medication packet is inserted on either side, to accommodate right and left hand users. This embodiment also provides ease in viewing the packet's transparent side to monitor inhalation of the medication.

FIG. 6a is a view of the preferred embodiment of the first valve 30. Initially, the flap 60a is essentially straight. The flap 60a moves down towards the hole 61 as the air is drawn in. The faster the air is drawn in, the more the flap 60a moves towards the hole 61, to limit the amount of air flow. A stop 62 prevents the flap from covering the hole 61 completely. 60b shows the flap during operation.

FIG. 6b shows an alternative embodiment of the first valve 30. This embodiment has a disc 63 attached to struts 64. As air is sucked in, the disc 63 moves towards the hole 61 to limit air flow.

It is clear from the foregoing, that the present invention creates a highly improved inhaler and medicated packet.

What is claimed:

1. A combination for administration of powdered medication comprising:
   a) an inhaler having an essentially cylindrical body member having,
      1) a slot located in said body member,
      2) a mouthpiece located at a first end of said body member,
      3) an end piece located at a second end of said body member; and,
   b) a medicated packet insertable into said slot in said body member and having,
      1) a blister side panel having a raised envelope containing a powdered medication,
      2) an essentially flat side panel sealing said raised envelope and having at least two holes therein and aligned to communicate with said envelope such that, in operation, patient supplied inhalation air flows through one hole into said envelope entraining said powdered medication and transporting said powdered medication out the other hole to the inhaling patient via said mouthpiece, and,
      3) a removable layer affixed to said flat side panel and completely covering said holes.

2. The combination according to claim 1 wherein said removable layer maintains dryness of said powdered medication.

3. The combination according to claim 2 wherein a portion of said blister packet is transparent for operator viewing of the amount of said powdered medication dispensed.

4. The combination according to claim 1 further including a cap for covering all of said body member except said endpiece.

5. The combination according to claim 4 wherein, after removal of said cap, said cap includes an attachment means for attaching one end of said cap onto said endpiece.

6. The apparatus according to claim 1 wherein said body member is comprised of three modules, said modules detachable from each other, for cleaning of said inhaler.

7. The combination according to claim 1 wherein said inhaler includes a first valve means for modulating air flow through and inhaler and wherein said inhaler further including holes located around the circumference of said body member, said holes located upstream from said first valve means and downstream from said endpiece, for allowing air to enter said inhaler.

8. The combination according to claim 6 wherein said inhaler further including a first valve, said first valve positioned to limit maximum airflow through said inhaler to the patient.

9. The combination according to claim 6 wherein said inhaler includes an inner channel for airflow therethrough, said inner channel located in said inhaler downstream of said first valve.

10. The combination according to claim 9 wherein said inner channel follows a curving path, for creating turbulent airflow, and abrasion of the medication against the channel walls.

11. The combination according to claim 9 further including a second valve for restricting air flow to one direction, said second valve positioned down stream of said inner channel.

12. A powdered medicant inhalation device comprising:
   a) A tube shaped housing having,
      1) a slot, located in said housing and a single dose medicational packet positioned in said slot such that a portion of airflow created by a patient's inhalation through said housing passes through said single dose medicational packet,
      2) a mouthpiece located at a first end of said housing;
   b) an essentially disk shaped first valve means for limiting airflow through said housing, said first valve means positioned towards a second end of said housing; and,
   c) an inner airflow channel means for allowing airflow through said housing, said inner channel means located between said slot and said mouthpiece.

13. The inhalation device according to claim 12 wherein said housing includes an endpiece located at the second end of said housing and further including a cap means for covering all of said housing except said endpiece.

14. The inhalation device according to claim 13 wherein said cap includes attachment means for attaching one end of said cap to said endpiece.

15. The inhalation device according to claim 12 wherein said housing is comprised of three detachable segments.

16. The inhalation device according to claim 12 wherein said device has holes located around a circumference of said housing and communicating with said inner airflow channel means.

17. The inhalation device according to claim 15 wherein said first valve means has a movable flap member on one side and an airflow hole on the other side, said movable flap partially blocking said airflow hole during inhalation by a patient through said mouthpiece.

18. The inhalation device according to claim 17 wherein said first valve means has a stop to prevent said flap means from covering said hole completely.

19. The inhalation device according to claim 16 wherein said inner airflow channel means is a curving path inside of said housing for creating abrasion of said medication.

20. The inhalation device according to claim 12 further including a second valve means for restricting air flow to one direction, said second valve means positioned downstream of said inner channel.

21. The inhalation device according to claim 20 wherein said second valve means has movable flaps members, said movable flap members opening when airflow is towards said mouthpiece and said flap members closing when airflow is reversed.

* * * * *